(12) United States Patent
Kim

(10) Patent No.: US 8,668,941 B2
(45) Date of Patent: Mar. 11, 2014

(54) **METHOD FOR PREPARING SUPPLEMENT USING PETTITOES OR PIG'S HEAD AND *ZANTHOXYLUM PIPERITUM*, AND COMPOSITION THEREOF**

(76) Inventor: Chun Gi Kim, Yeongyang-gun (KR)

( * ) Notice: Subject to any disclaimer, the term of this patent is extended or adjusted under 35 U.S.C. 154(b) by 0 days.

(21) Appl. No.: 13/884,974

(22) PCT Filed: Jul. 28, 2011

(86) PCT No.: PCT/KR2011/005559
§ 371 (c)(1),
(2), (4) Date: May 13, 2013

(87) PCT Pub. No.: WO2012/086893
PCT Pub. Date: Jun. 28, 2012

(65) Prior Publication Data
US 2013/0259950 A1 Oct. 3, 2013

(30) Foreign Application Priority Data

Dec. 20, 2010 (KR) ........................ 10-2010-0130730

(51) Int. Cl.
*A01N 65/00* (2009.01)
(52) U.S. Cl.
USPC ........................................................ 424/725
(58) Field of Classification Search
None
See application file for complete search history.

(56) References Cited

FOREIGN PATENT DOCUMENTS

| KR | 10-315718 B1 | 2/2002 |
|---|---|---|
| KR | 10-2007-0005354 A | 1/2007 |
| KR | 10-0666310 B1 | 1/2007 |

OTHER PUBLICATIONS

International Search Report Issued in PCT/KR2011/005559, mailed on Mar. 16, 2012.

*Primary Examiner* — Michael Meller
(74) *Attorney, Agent, or Firm* — Birch, Stewart, Kolasch & Birch, LLP

(57) ABSTRACT

The present invention relates to a dietary supplement capable of treating and preventing symptoms of immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like. More specifically, the dietary supplement is prepared by the following steps: preparing pettitoes or a pig's head in cold water for about 24 hours to remove blood and to wash the same; preparing *Zanthoxylum piperitum* by collecting, selecting, and washing the branches and fruits of the *Zanthoxylum piperitum*; heating a mixture comprising the prepared pettitoes or pig's head and the branches and fruits of *Zanthoxylum piperitum* and water in a water bath at 150° C. to 250° C. for about 10 hours; filtering the extract heated in a water bath with a filter and mixing the extract and maple syrup; and boiling the filtered extract at 100° C. for 5 minutes and packaging the same into a pouch.

1 Claim, 1 Drawing Sheet

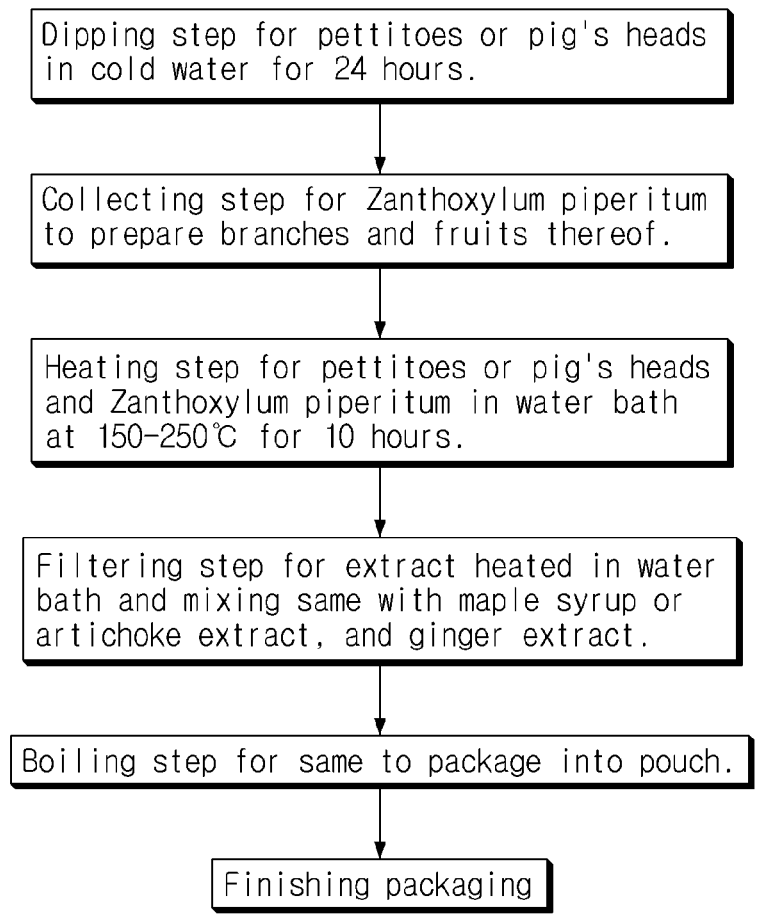

METHOD FOR PREPARING SUPPLEMENT USING PETTITOES OR PIG'S HEAD AND ZANTHOXYLUM PIPERITUM, AND COMPOSITION THEREOF

TECHNICAL FIELD

The present invention relates to a dietary supplement that is capable of treating and preventing symptoms of immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like. More specifically, the present invention relates to a method for preparing a dietary supplement using pettitoes or a pig's head, and *Zanthoxylum piperitum*, that is capable of preventing diseases and maintaining health by removing excessive dampness in the body and a cold chill in the bone-marrow by taking an extract twice a week, wherein the extract is obtained by selecting one or more of pettitoes, a pig's head, *Zanthoxylum piperitum*, maple syrup, ginger, and artichoke and heating the selected mixture for about 10 hours, and a composition thereof.

BACKGROUND ART

Various dietary supplements that are helpful for atopic disease patients or degenerative arthritis patients have been supplied till now. However, such dietary supplements are mainly composed of a mixture of grain or medicinal herbs, and many kinds of materials are mixed therein and thus, such dietary supplements are provided at high prices. Further, since these dietary supplements are composed of grain and medicinal herbs, and the amount of grain and medicinal herbs to be supplied varies depending on environmental and climatic conditions of cultivated fields and therefore the grain and medicinal herbs cannot be supplied constantly, they may cause a great fluctuation in prices of produced dietary supplements.

According to prior arts in the field of the present invention, Korean Patent Laid-open Publication No. 2006-0132536 (Prior Art 1) entitled "Dietary supplement for atopic skin diseases" describes a dietary supplement that is extracted from a mixture of 10 parts by weight of Membranous Milkvetch root, 4 parts by weight of cinnamon, 4 parts by weight of *Glycyrrhiza uralensis* Fisch., 6 parts by weight of kudzu-vine, 6 parts by weight of *Poncirus trifoliata* Raf, 10 parts by weight of barbary wolfberry fruit, 5 parts by weight of *Gigantic Angelica*, 10 parts by weight of *Arnebia guttata* Bunge, 6 parts by weight of *Pleuropterus multiflorus* TURCZ., 5 parts by weight of Japanese atracty-lodes, 5 parts by weight of Baikal skullcap, 6 parts by weight of dan-shen, 5 parts by weight of *Cnidium officinale* Makino, 5 parts by weight of *Paeonia lactiflora*, 10 parts by weight of *Morus alba* L., 10 parts by weight of *Thuja orientalis* L., 8 parts by weight of burdock, 3 parts by weight of Chinese magnolia vine, 5 parts by weight of *Wolfiporia cocos*, 6 parts by weight of evening primrose, 9 parts by weight of Chinese lizardtail, and 10 parts by weight of perennial artemisia.

Korean Patent Laid-open Publication No. 2005-0003173 (Prior Art 2) entitled "Compositions of dietary supplement to treat osteoarthritis" relates to a dietary supplement containing medicinal herbs to treat osteoarthritis, wherein the dietary supplement described therein includes 40 to 50% by weight of glucosamine, 20 to 30% by weight of mucopolysaccharide-protein, 5 to 10% by weight of vitamin C, 1 to 5% by weight of vitamin E, 5 to 10% by weight of shark cartilage powder, 3 to 7% by weight of *achyranthes* root extract powder, 3 to 7% by weight of quince extract powder, 1 to 2% by weight of eucommia bark extract powder, and 1 to 2% by weight of sucrose fatty acid ester.

As can be seen from Prior Arts 1 and 2, the respective dietary supplements are comprised of too many kinds of materials mixed therein. It can be seen that too many medicinal herbs are used in Prior Art 1, and too many expensive materials are used in Prior Art 2. Prior Arts 1 and 2 are far from practical in terms of production cost, profit, and consumer price. That is, it is obvious that if the above-described materials are used for producing the respective dietary supplements, the dietary supplements may be produced at high prices and sold to consumers at higher prices. Therefore, in order to produce these dietary supplements at purchasable prices for consumers, insufficient compositions of extracts may be used. In particular, as for the shark cartilage powder, the *achyranthes* root extract powder, and the like, raw materials required to get a desired effect cannot be supplied sufficiently during production.

Further, if a dietary supplement is comprised of more compositions than necessary, an initial effect can be increased, but long-term use of the dietary supplement may cause a decrease in a body's immune function of relieving a disease and a curative effect of the dietary supplement. Thereafter, a desired medicinal effect can be obtained only when a stronger substance is used. Accordingly, such a dietary supplement is not helpful for humans in the long term.

DISCLOSURE

Technical Problem

To solve the above problems, the present invention provides a dietary supplement by selecting one or more of pettitoes, or a pig's head, *Zanthoxylum piperitum*, maple syrup, ginger, and artichoke, and extracting from a mixture of pettitoes, or a pig's head, *Zanthoxylum piperitum*, and maple syrup; a method for preparing a dietary supplement using pettitoes or a pig's head, and *Zanthoxylum piperitum* to maintain health with a dietary supplement including pettitoes or a pig's head, *Zanthoxylum piperitum*, ginger, and artichoke which is capable of removing a cold chill in the bone-marrow which is origin of many illnesses, supporting the circulation system, and preventing immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like; and a composition thereof

Technical Solution

In order to achieve the above object, the present invention is provided to remove a cold chill from the body and the bone-marrow to prevent immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like.

In order to prevent symptoms of the above-described diseases, an exemplary embodiment of the present invention provides a method in which a mixture comprised of pettitoes or a pig's head, and branches and fruits of Zanthoxylum piperitum and water are put into a water bath and heated at about 150° C. to about 250° C. for about 10 hours, and an extract thereof is mixed with extracts of ginger and artichoke and heated.

A resultant extract is packaged into a pouch. Thus, it is possible to provide a method for preparing a dietary supplement using pettitoes or a pig's head and Zanthoxylum piperitum, and a composition thereof, wherein the dietary supplement is helpful for preventing the above-described diseases by taking about 250 ml to about 300 ml of the extract twice a week in the case of an adult.

Effect of the Invention

The present invention provides a dietary supplement helpful in treating and preventing immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like thereby maintaining health.

DESCRIPTION OF DRAWINGS

FIG. 1 is a diagram illustrating a preparing process in accordance with the present invention.

BEST MODE

The present invention is characterized by: preparing pettitoes or a pig's head by soaking them in cold water for about 24 hours to remove blood from them and washing the same;

preparing Zanthoxylum piperitum by collecting, sorting, and washing branches and fruits of Zanthoxylum piperitum;

heating a mixture of the prepared pettitoes or pig's head, the branches and fruits of Zanthoxylum piperitum and water in a water bath at about 150° C. to about 250° C. for about 10 hours;

filtering the extract heated in the water bath with a filter and mixing the extract with maple syrup;

and boiling the filtered extract at about 100° C. for about 5 minutes and packaging the same into a pouch.

The mixture at the step of heating a mixture is prepared by putting a mixture of the pettitoes or the pig's head, and the branches and fruits of Zanthoxylum piperitum, ginger, and artichoke with the water into the water bath and heating therein at about 150° C. to about 250° C. for about 10 hours, and obtaining the extract.

The extract obtained as described above is packaged into a pouch. Thus, it is possible to provide a method for preparing a dietary supplement using pettitoes or a pig's head, and Zanthoxylum piperitum, and a composition thereof, wherein the dietary supplement is helpful for preventing immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like by taking about 250 ml to about 300 ml of the extract twice a week in the case of an adult.

Hereinafter, exemplary embodiments of the present invention will be explained in detail as follows.

First Step: Preparation of Materials

1. Pettitoes

Front legs and hind legs of a pig are purchased, and hairs remaining on their skin are removed. Then, they are soaked in cold water for about 24 hours to remove foreign materials and blood.

The legs that are immersed for removal of blood are washed clean and prepared as pettitoes.

1-1. Pig's Head

A pig's head is purchased, and hairs remaining on its skin are removed. Then, it is immersed in cold water for about 24 hours to remove blood and foreign materials remaining in the ears and the mouth.

The pig's head that is immersed for removal of blood and foreign materials is washed clean.

2. Zanthoxylum piperitum

Zanthoxylum piperitum is a scientific name of Japanese pepper.

Zanthoxylum piperitum is full of fruits in June and the fruits turn red around August although it may vary from region to region. In late August, the red fruits are ripe and the skin begins to peel off.

Zanthoxylum piperitum grows on hillsides or mountain valleys and has a height of about 3 m to about 5 m. Pairs of sharp thorns changed from cotyledons are grown below respective petioles and the sharp thorns slightly bend downwards. A branch has odd-pinnately compound leaves alternately arranged. Each leaf is small and oblong-ovate with about 4 to 7 crenate margins. There are gland points under the crenate margins. The leaf has a yellow-green pattern at a central part thereof and has a strong scent.

Zanthoxylum piperitum blooms in May to June, forming axillary flower clusters. The flowers are unisexual, corymbose, and yellow-green in color. Each flower has five sepals. A male flower has five stamens, whereas a female flower has an ovary separated from two styles. Each fruit splits up into two mericarps. The fruits turn red around September and scatter black seeds. Young leaves of Zanthoxylum piperitum are edible, and the fruits are used to make medicine or seasoning. Peels of the fruits are used as a spice. In Gyeongsang Provinces of Korea, Zanthoxylum piperitum is called "zeppy tree" and peels of fruits are called "zeppy" and also called "gocho" in the countryside. In Gyeongsang Provinces, such peels are ground and sprinkled on a broiled loach dish (called "chueotang" in Korea) as a spice for removing a fishy smell of loaches. The peels have a spicy flavor and a pungent smell and are more commonly used in Japan than in Korea. In Japan, the fruits are commercialized as a spice called sansai, sansho or kinome, and often used for meat dishes and fish dishes.

Branches and fruits of Zanthoxylum piperitum having the above-described properties are collected and clean ones are selected.

Second Step: Heating Process

1. Mixing Materials

ⓐ Mixing materials that are helpful in treating and preventing viral diseases (cold, varicella, and herpes zoster), musculoskeletal diseases (arthritis, traffic accident sequela, sciatica, frozen shoulder, and herniated disk), and neurological diseases (insomnia, menopausal disorder, hypothermia, cold hands and feet, dysautonomia, and postpartum pain)

The prepared pettitoes or pig's head, branches and fruits of Zanthoxylum Piperitum, and water are put into a water bath and heated at about 150° C. to about 250° C. for about 10 hours.

ⓑ Mixing materials that are helpful in treating and preventing immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), and neurological diseases (insomnia, menopausal disorder, hypothermia, cold hands and feet, dysautonomia, and postpartum pain) in accordance with another exemplary embodiment The prepared pettitoes or pig's head, branches and fruits of *Zanthoxylum Piperitum*, and water are put into a water bath and heated at about 150° C. to about 250° C. for about 10 hours.

Third Step: Filtering and Boiling Processes

A liquid extract obtained from the materials in the water bath of the step ⓐ or ⓑ is filtered with a filter to obtain a pure liquid extract.

The filtered liquid extract is mixed with maple syrup or an artichoke extract and a ginger extract in a boiling container and boiled at about 100° C. for about 5 minutes. Then, the boiled extract is packaged into a pouch by using a packaging machine.

The pouch packaging is carried out at about 100° C. or higher, and, thus, the extract is vacuum-packaged due to such a high temperature at the time of packaging.

The pouch packaged as described above can be stored for a long time.

Hereinafter, exemplary embodiments will be explained in detail based on the above-described preparing process.

Embodiment 1

Embodiment 1 provides a dietary supplement effective against viral diseases (cold, varicella, and herpes zoster), musculoskeletal diseases (arthritis, traffic accident sequela, sciatica, frozen shoulder, and herniated disk), and neurological diseases (insomnia, menopausal disorder, hypothermia, cold hands and feet, dysautonomia, and postpartum pain). Hereinafter, the dietary supplement will be referred to as "Haeryeong Cheonda 1".

1) Preparation of Materials
Pettitoes: two front legs and two hind legs
Two pigs' heads
*Zanthoxylum piperitum*: branches of about 4 kg and fruits in two 300 cc cups
Maple syrup: about 1.5 liters
Water: about 50 liters The pettitoes or pigs' heads have been immersed in cold water for about 24 hours to remove foreign materials and blood as described above.

2) Heating

All the prepared materials are put into a water bath and heated at about 150° C. for about 10 hours.

The water bath is one of typically used water baths. Even if the water of about 50 liters is heated in the water bath for about 10 hours, the heating step is continuously performed without leaking steam. Thus, bones of the pettitoes or pigs' heads are totally softened and remain as sludge lumps after being pressured, and a liquid is discharged through a discharge hole at a side of the water bath.

3) Filtering, and Packaging in a Heated State

An extract obtained from the water bath is filtered with a filter to remove the sludge and boiled in a heating container at about 100° C. or higher. While being boiled at about 100° C. or higher, the extract is transferred to a pouch packaging machine to be packaged into a pouch.

The extract heated by a heater is packaged in the pouch packaging machine. Thus, oxygen is removed instantaneously from the inside of the pouch due to such a high temperature and the inside of the pouch can be maintained in a vacuum.

The extract pouch that is vacuum-packaged as described above can be stored for about 3 months or longer in a place away from direct sunlight.

Embodiment 2

Embodiment 2 provides a dietary supplement effective against immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), and neurological diseases (insomnia, menopausal disorder, hypothermia, cold hands and feet, dysautonomia, and postpartum pain). The dietary supplement is produced in the same manner as described in Embodiment 1 except some materials included therein. Hereinafter, the dietary supplement of Embodiment 2 will be referred to as "Haeryeong Cheonda 2".

1) Preparation of Materials
Pettitoes: two front legs and two hind legs
Two pigs' heads
Zanthoxylum piperitum: branches of about 4 kg and fruits in two 300 cc cups
Artichoke extract: about 300 cc
Ginger extract: about 120 cc
Water: about 50 liters The artichoke extract and the ginger extract are prepared by using a separate juice extractor and a heating container, respectively. The artichoke extract of about 300 cc is prepared by extracting from artichoke with the juice extractor, and the ginger extract of about 120 cc is prepared from ginger and water by heating in the heating container for about 2 hours to about 3 hours.

If the artichoke and the ginger are heated for about 10 hours together with the pettitoes or pigs' heads, nutrients thereof may be destroyed. Therefore, the reason why the artichoke extract and the ginger extract are prepared as described above is to prevent destruction of nutrients of the artichoke and the ginger.

2) Heating

The materials are heated in the same manner as described in Embodiment 1. The two front legs and two hind legs or the two pigs' heads, the *Zanthoxylum piperitum* branches of about 4 kg and fruits in two 300 cc cups, and the water of about 50 liters are put into a water bath and heated for about 10 hours.

Further, the artichoke extract of about 300 cc is prepared by extracting from artichokes with the juice extractor, and the ginger extract of about 120 cc is prepared from materials in a ratio of water of about 300 cc and ginger of about 10 g by heating in the heating container for about 2 hours to about 3 hours.

3) Filtering and Heating

In the same manner as described in Embodiment 1, an extract obtained from the water bath is mixed with the artichoke extract of about 300 cc and the ginger extract of about 120 cc, and filtered with a filter and then boiled in a boiling container at about 100° C. While being boiled at about 100° C., the mixture is packaged into a pouch.

Hereinafter, some clinical tests performed with the products prepared as described above will be explained.

Test groups include a group of six arthralgic patients (Group A), a group of four skin disease patients (Group B), a group of four abdominal pain patients (Group C), and a group of four respiratory disease patients (Group D).

These patients of these test groups were checked and treated at a hospital but their conditions were not considerably improved. Then, they participated in the clinical tests and took the dietary supplements of the present invention at an oriental medical clinic "Saam Achim" in Sanbon, Gyeonggi Province of Korea.

<Test 1> Arthralgic Patients (Group A)

Group A includes two 50-year-old female patients with general arthralgia, one 49-year-old female patient with arthralgia, and a 8-year-old male patient with growth pain and reduced immunity. About 240 ml to about 300 ml of "Haeryeong Cheonda 1" prepared in Embodiment 1 was administered orally to the patients of Group A.

① One of the two 50-year-old female patients with general arthralgia felt pains in the neck, back, arms, fingers, and wrists and gained weight. Her body was bloated, her digestion was not good and her mouth was often dry. She had constipation.

"Haeryeong Cheonda 1" was administered to her once a week. In the second week, she started feeling reduced pains when she was awoken in the morning, and in the tenth week, more than half of arthralgia was reduced and a cold chill was removed from her body. After the twentieth week, her condition was improved to a degree almost not to feel arthralgia.

② The other 50-year-old female patient with general arthralgia had pains in the nose, knees, fingers, soles, and toes and often had a stomachache. She had hard stools. She had a fever in the hands and feet and often had nasal congestion. Further, her hands and feet often stiffened and were cold.

"Haeryeong Cheonda 1" was administered to her twice a week. After the fourth week administration, her hands became warm and soft. After the tenth administration, pains in the fingers and soles were removed. Her feet could be kept warm and her stiff hands and stiff neck were much relieved to a degree sufficient not to feel any problem in her daily life.

③ The 49-year-old female patient with arthralgia had arms feeling weak and heavy. She had aches and pains all over her body and felt a cold chill. She sometimes felt dizzy and dazy. She often had a fever and a headache. Further, she had tinnitus.

"Haeryeong Cheonda 1" was administered to her three times a week. After the second week, her condition was so much improved that she could feel better. Thereafter, she took "Haeryeong Cheonda 1" once a week. Now, she does not have pains during sleep.

④ The 8-year-old male patient with growth pain and sleeptalking felt full even if he ate something small, and easily caught a cold during the change of seasons. He suffered from leg myalgia. Further, it was difficult for him to fall into a deep sleep.

"Haeryeong Cheonda 1" was administered to him twice a week. After the fourth week administration, he did not suffer from leg myalgia. Further, he could fall into a deep sleep, overcoming fatigue.

It could be seen that all the patients of Group A were improved after the second week of administration of "Haeryeong Cheonda 1". After the fourth week of administration, growth pain almost disappeared and arthralgia was relieved. The patients with administration of "Haeryeong Cheonda 1" for 10 weeks or longer were improved and almost completely cured.

This clinical test shows that "Haeryeong Cheonda 1" of the present invention helps arthralgic patients to be cured and also to improve and maintain their health.

<Test 2> Skin Disease Patients (Group B)

Group B includes one 18-year-old male patient with an atopic disease, one 20-year-old female patient with eczema, one 35-year-old female patient with uredo, and one 15-year-old female patient with a skin disease. About 240 ml to about 300 ml of "Haeryeong Cheonda 1" prepared in Embodiment 1 was administered orally to the patients of Group B.

① The 18-year-old male patient with an atopic disease felt full even if he ate something small. He had hard stools. Atopic symptoms could be observed in his overall body, especially in the head, trunk, and limbs at his first visit to the clinic.

"Haeryeong Cheonda 1" was administered to him twice a week. After the sixth week administration, he was remarkably improved, and after the eighth month of administration, symptoms of his atopic disease were reduced by about 80% or more.

② The 20-year-old female patient with eczema had a red rash on the face. After being washed, her face was flushed with fever. She had no appetite and felt full shortly after eating. She had soft stools. She often had palpitations and had irregular menstruation.

"Haeryeong Cheonda 1" was administered to her once per five days. After the third month of administration, her face was not flushed with fever after being washed and did not feel full shortly after eating. After the sixth month of administration, she had normal stools and had regular menstruation. A red rash and eczema were almost removed enough not to feel any problem in her daily life.

③ The 35-year-old female patient with uredo felt itchy all over her body and could not sleep well. She did not have plenty of breast-feed milk. Although she had a good digestion and a good appetite, she had hard stools and urinated twice at night. After waking up at night, she had trouble in falling asleep again. She easily had a feeling of fatigue and had pains in the nape, wrists, knees, ankles, and back. Further, she had irregular menstruation.

"Haeryeong Cheonda 1" has been administered to her once per five days. After the fifth administration, she could fall into a deep sleep and did not wake up at night to urinate. After the tenth administration, she felt less itchy and did not have a feeling of fatigue easily. Further, she had regular menstruation.

④ The 15-year-old female patient with a skin disease had atopic symptoms on her face and folded areas on the arms and legs. Although she had a normal digestion, she felt a pressure on her chest. She often urinated and had a fever, especially, at night.

"Haeryeong Cheonda 1" was administered to her twice a week continuously for two months. Thereafter, atopic symptoms were almost removed with a slight scar. She did not have a fever. Further, although she slightly felt itchy at night, she did not feel itchy in the day time. She was improved enough not to feel any problem in her daily life.

As a result of the administration of "Haeryeong Cheonda 1" to the patients of Group B, it could be seen that "Haeryeong Cheonda 1" was also effective for skin disease patients.

In particular, for the patients with an atopic disease which has been regarded as an incurable disease, "Haeryeong Cheonda 1" was effective after the second month of administration. They were much improved and seem to be cured to a greater or lesser extent if they continuously take "Haeryeong Cheonda 1".

Further, "Haeryeong Cheonda 1" was considerably effective against a skin disease and eczema after long-term administration for several months. After ten months or longer of administration, the patients were almost completely cured.

<Test 3> Abdominal Pain Patients (Group C)

Group C includes one 30-year-old female patient with gastritis and abdominal pain, one 21-year-old female patient with abdominal pain, one 54-year-old female patient with back pain and earreflexology, and one 16-year-old female patient with enuresis. About 240 ml to about 300 ml of "Haeryeong Cheonda 2" prepared in Embodiment 2 was administered orally to the patients of Group C.

① The 30-year-old female patient with gastritis and abdominal pain felt full even if he ate something small. She had a bloated stomach and easily caught a cold during the change of seasons. She had cold hands and feet. Her stomach was sensitive to cold foods. She often felt pains in the nape and back. Further, she had chronic gastritis and reflux esophagitis. She often had diarrhea.

"Haeryeong Cheonda 2" was administered to her once a week to remove a cold chill from the small intestine. She ended the clinical test with the fourth administration.

After the fourth administration, she did not have a stomachache and diarrhea any longer. Her gastritis was relieved enough not to feel any problem in her daily life. Although her gastritis was not completely cured, it could be seen that she was much better than before the administration of "Haeryeong Cheonda 2".

② The 21-year-old female patient with abdominal pain often went to the toilet whenever she had a meal. She went to the clinic for stiff stomach after taking medicine for cleaning the bowels and was prescribed "Haeryeong Cheonda 2" once a week for her bloated bowels and constipation caused by gas in the bowels. After the fourth administration, she began to have diarrhea but had normal stools as time went by. Her bowel condition was considerably improved. Although long-term administration was recommended to her, she stopped administration thereafter and progress of her bowel condition could not be observed.

③ The 54-year-old female patient with back pain and earreflexology felt full even if she ate something small and had constipation. Her hands and feet were often bloated and she had pains in the nape, shoulders, and back. She had a pain in the back for about 30 years, but there was no significant improvement despite many times of treatment.

"Haeryeong Cheonda 2" was administered to her twice a week for four weeks. As a result of the administration, pains were reduced when she stretched her back, and a cold chill was much removed from the pelvis.

After the eighth week of continuous administration, she felt no pains in the back when moving, and a severe pain in the back that she felt when sitting in a car for a long time was completely removed.

Further, the cold chill was completely removed from the pelvis.

④ The 16-year-old female patient with enuresis had no problem in appetite, digestion and had normal stools. However, she urinated twice or more/night in her sleep. Further, she often had a headache and often felt a pressure on her chest. After waking up, she felt dopey.

"Haeryeong Cheonda 2" was administered to her twice a week for four weeks. After the eighth administration, enuresis was cured. For three years after the administration, she has not experienced a recurrence of enuresis.

<Test 4> Respiratory Disease Patients (Group D)

Group D includes one 38-year-old female patient who easily catches a cold and feels a pressure on her chest, one 29-year-old male patient with rhinitis and insomnia, one 9-year-old male patient with a runny nose and nasal conges-tion, and one 11-year-old male patient with rhinitis and a sore throat. About 240 ml to about 300 ml of "Haeryeong Cheonda 2" prepared in Embodiment 2 was administered orally to the patients of Group D.

① The 38-year-old female patient who easily catches a cold and feels a pressure on her chest had indigestion and often had a stomachache. She often burped and had a bloated stomach. Further, she had soft stools and easily had a feeling of fatigue.

"Haeryeong Cheonda 2" was administered to her once a week for three weeks. After the administration, symptoms of a cold were relieved, and she did not have a feeling of fatigue, a fever, and stomatitis.

② The 29-year-old male patient with rhinitis and insomnia continuously had nasal congestion when waking up due to rhinitis, insomnia, lack of sleep, chronic fatigue and ringing in the ears. He could not fall asleep at night and had a nightmare in his sleep.

"Haeryeong Cheonda 2" was administered to him once a week. After the fourth administration, his rhinitis was cured and he could sleep well. As his body could be kept warm, his chronic fatigue was relieved.

③ The 9-year-old male patient with a runny nose and nasal congestion liked cold water and often felt very thirsty. He had severe constipation and often urinated. Further, he had a severe runny and stuffy nose with sneezing.

"Haeryeong Cheonda 2" was administered to him once per five days for a month. After the administration, his rhinitis was cured and he could sleep well. After further administration for a month, his nasal congestion was relieved. As his body could be kept warm, he did not often urinate and could retain his urine.

④ The 11-year-old male patient with rhinitis and a sore throat had no appetite and felt the cold badly and often had a fever. Further, he often had a runny nose and had chronic rhinitis.

"Haeryeong Cheonda 2" was administered to him once a week for four weeks. After the administration, his respiratory symptoms were completely removed and he had a good appetite. After further administration for a month, a temperature at the ends of his limb was increased to be almost equal to that of a normal person and his rhinitis was completely cured.

The present applicant, KIM, Chun Gi, has studied the dietary supplements for many years and supplied them to the oriental medical clinic. The above-described results of the clinic tests performed in the oriental medical clinic show the curative influence of the dietary supplements.

As described above, the dietary supplements, Haeryeong Cheonda 1 and 2, using pettitoes or a pig's head, and *Zanthoxylum piperitum* of the present invention are highly effective in treating and preventing symptoms of immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), neurological diseases (insomnia, menopausal disorder, hypothermia, cold hands and feet, dysautonomia, and postpartum pain), and the like.

That is, the above-described diseases are caused by cold chill in the body and a cold wind penetrating into the bone-marrow, and, thus, by removing excessive coldness in the body and a cold chill (cold wind) in the bone-marrow as origin of many illnesses, the blood circulation can be improved and the nervous system can function well and spinal nerves and peripheral nerves can also function well. Thus, it is possible to treat and prevent immune diseases (reduced immunity, allergic disease, and respiratory disease), viral diseases (cold, varicella, and herpes zoster), musculoskeletal diseases (arthritis, traffic accident sequela, sciatica, frozen shoulder, and herniated disk), and neurological diseases (insomnia, menopausal disorder, hypothermia, cold hands and feet, dysautonomia, and postpartum pain) and also possible to maintain health.

In the present invention, the dietary supplement is prepared by using pettitoes, a pig's head, Zanthoxylum piperitum, maple syrup, ginger, and artichoke, and, thus, many people can use this dietary supplement inexpensively and also maintain their health.

Further, the materials used in the present invention can be easily supplied in large amounts from almost anywhere in the country, and, thus, the dietary supplement can be readily supplied at a stable price in response to customer demand.

INDUSTRIAL APPLICABILITY

The present invention provides a dietary supplement effective against immune diseases such as reduced immunity, allergic disease, and respiratory disease, viral diseases such as cold, varicella, and herpes zoster, musculoskeletal diseases such as arthritis, traffic accident sequela, sciatica, frozen shoulder, and herniated disk, and neurological diseases such as insomnia, menopausal disorder, hypothermia, cold hands and feet, dysautonomia, and postpartum pain, and allows climacteric adults to easily buy and take the dietary supplement from oriental medical clinics, hospitals, pharmacies, and the like. Therefore, the present invention can contribute to improvement in national health and enables many people to enjoy their later years.

The invention claimed is:

1. A method for preparing a dietary supplement comprising:
   soaking pettitoes or pig's head in cold water for about 24 hours to remove blood and washing the same to yield a prepared pettitoes or pig's head;
   preparing Zanthoxylum piperitum by collecting, sorting, and washing branches and fruits of the Zanthoxylum piperitum;
   heating a mixture of the prepared pettitoes or pig's head, the branches and fruits of Zanthoxylum piperitum and water in a water bath at about 150° C. to about 250° C. for about 10 hours to yield a pettitoes or a pig's head and Zanthoxylum piperitum extract;
   filtering the pettitoes or a pig's head and Zanthoxylum piperitum extract with a filter and then mixing the extract either with maple syrup or with an artichoke extract and a ginger extract to yield a filtered extract; and
   boiling the filtered extract at about 100° C. for about 5 minutes and packaging the same into a pouch to yield said dietary supplement.

* * * * *